(12) United States Patent
Chien et al.

(10) Patent No.: US 7,887,848 B2
(45) Date of Patent: Feb. 15, 2011

(54) NUTRACEUTICAL TREATMENTS FOR DIABETIC AND NON-DIABETIC WOUND HEALING

(75) Inventors: Xiaoming Xu Chien, Benicia, CA (US); Debasis Bagchi, Concord, CA (US)

(73) Assignee: Interhealth Nutraceuticals, Inc., Benicia, CA (US)

( * ) Notice: Subject to any disclaimer, the term of this patent is extended or adjusted under 35 U.S.C. 154(b) by 615 days.

(21) Appl. No.: 11/809,149

(22) Filed: May 31, 2007

(65) Prior Publication Data
US 2008/0003303 A1 Jan. 3, 2008

Related U.S. Application Data

(60) Provisional application No. 60/810,741, filed on Jun. 2, 2006, provisional application No. 60/809,542, filed on May 31, 2006.

(51) Int. Cl.
| | |
|---|---|
| A01N 59/00 | (2006.01) |
| A01N 39/00 | (2006.01) |
| A01N 59/16 | (2006.01) |
| A01N 55/02 | (2006.01) |
| A61K 33/00 | (2006.01) |
| A61K 33/40 | (2006.01) |
| A61K 33/32 | (2006.01) |
| A61K 33/24 | (2006.01) |
| A61K 31/28 | (2006.01) |
| A61K 31/315 | (2006.01) |

(52) U.S. Cl. ............... 424/641; 424/600; 424/614; 424/642; 424/655; 514/492; 514/494; 514/505

(58) Field of Classification Search ............... 424/600, 424/614, 641, 642, 655; 514/492, 494, 505
See application file for complete search history.

(56) References Cited

U.S. PATENT DOCUMENTS

| | | | |
|---|---|---|---|
| 4,923,855 | A | 5/1990 | Jensen |
| 4,954,492 | A | 9/1990 | Jensen |
| 5,047,249 | A | 9/1991 | Rothman et al. |
| 5,194,615 | A | 3/1993 | Jensen |
| 5,487,899 | A | 1/1996 | Davis |
| 5,637,321 | A | 6/1997 | Moore |
| 5,645,851 | A | 7/1997 | Moore |
| 5,750,144 | A | 5/1998 | Moore |
| 5,789,401 | A | 8/1998 | McCarty |
| 5,962,517 | A | 10/1999 | Murad |
| 5,972,999 | A | 10/1999 | Murad |
| 5,976,548 | A | 11/1999 | Hsia et al. |
| 5,976,568 | A | 11/1999 | Riley |
| 6,048,903 | A | 4/2000 | Toppo |
| 6,475,530 | B1 * | 11/2002 | Kuhrts .................. 424/725 |
| 6,579,543 | B1 | 6/2003 | McClung |
| 6,953,595 | B2 | 10/2005 | Basic et al. |
| 7,119,110 | B2 | 10/2006 | Bagchi et al. |
| 7,153,877 | B2 | 12/2006 | Bagchi et al. |
| 2002/0155138 | A1 | 10/2002 | Martin et al. |
| 2003/0026855 | A1 | 2/2003 | Kameneva et al. |
| 2004/0109905 | A1 | 6/2004 | Bagchi |
| 2005/0196359 | A1 | 9/2005 | D'Amelio et al. |
| 2005/0196470 | A9 | 9/2005 | Wuh et al. |
| 2005/0202101 | A1 | 9/2005 | Bagchi et al. |
| 2006/0009099 | A1 | 1/2006 | Jonn et al. |
| 2006/0024383 | A1 | 2/2006 | Berlin |
| 2006/0039937 | A1 | 2/2006 | Mujica-Fernaudd et al. |
| 2006/0062859 | A1 | 3/2006 | Blum et al. |

FOREIGN PATENT DOCUMENTS

| | | |
|---|---|---|
| WO | WO 2007/121312 | 10/2007 |
| WO | WO 2007/143002 | 12/2007 |
| WO | WO 2007/143631 | 12/2007 |

OTHER PUBLICATIONS

MacKay Douglas, Nutritional Support for Wound Healing, 2003, Alternative Medicine Review, vol. 8, No. 4, pp. 359-377.*
Bowler et al., "Wound microbiology and associated approaches to wound management," *Clin. Microbiol. Rev.*, 14:244-269 (2001).
Chen et al., "Evidence that the diabetes gene encodes the leptin receptor: identification of a mutation in the leptin receptor gene in db/db mice," *Cell*, 84:491-495 (1996).
Collins, "Diabetes, nutrition, and wound healing," *Adv. Skin Wound Care*, 16:291-294, (2003).
Hunt et al., "Oxygen: at the foundation of wound healing—introduction," *World J. Surg.*, 28:291-293 (2004).
Roy et al., "Dermal wound healing is subject to redox control," Mol. Ther., 13:211-220 (2006).

(Continued)

*Primary Examiner*—Johann R Richter
*Assistant Examiner*—Luke E Karpinski
(74) *Attorney, Agent, or Firm*—Marshall, Gerstein & Borun LLP

(57) ABSTRACT

In an embodiment of the present invention, a nutraceutical formula comprising a combination of chromium, zinc, berry extract, *Polygonum cuspidatum* extract, aloe vera, chlorophyll and L-arginine combined synergistically to reduce inflammation in mammals suffering from diabetes. In another embodiment of the present invention, a nutraceutical formula comprising a of zinc, chromium, berry extract, *Polygonum cuspidatum* extract, aloe vera, chlorophyll and L-arginine combined synergistically to enhance wound healing in mammals suffering from diabetes. In an alternative embodiment of the present invention, a nutraceutical formula comprising a of zinc, chromium, berry extract, *Polygonum cuspidatum* extractive, aloe vera, chlorophyll and L-arginine combined synergistically to reduce inflammation in mammals not suffering from diabetes. In another embodiment of the present invention, a nutraceutical formula comprising a combination of zinc, chromium, berry extract, *Polygonum cuspidatum* extractive, aloe vera, chlorophyll, and L-arginine combined synergistically to enhance wound healing in mammals not suffering from diabetes.

2 Claims, 1 Drawing Sheet

OTHER PUBLICATIONS

Albina et al., "Temporal expression of different pathways of l-arginine metabolism in healing wounds," *J. Immunol*; 144(10):3877-80 (1990).

Babu et al., "Estimation of trans-resveratrol in herbal extracts and dosage forms by high-performance thin-layer chromatography," *Chem Pharm Bull (Tokyo)* 53(6):691-3 (2005).

Bagchi et al., "Angiogenic and anti-angiogenic properties of natural polyphenolic antioxidants," *IFT Annual Meeting-Chicago Session 32, Angiogenesis and functional feeds* (2003).

Barrett at al., "Neurodegeneration and diabetes: UK nationwaide study of Wolfram (DIDMOAD) syndrome," *Lancet* 346(8988):1458-63 (1995).

Brett et al., "Chlorophyllin—A healer?" a Hypothesis for its Activity, *Wounds* 17(7):190-1 (2005).

Burns et al., "Plant Foods and Herbal Sources of Resveratrol," *J. Agric. Food Chem* 50(11): 3337-3340 (2002).

Chen et al., "Synthesis and Anti-inflammatory Activity of Resveratrol Analogs," *Chem. Pharm Bull* 53(12): 1587-1590 (2005).

Egner et al., "Chlorophyllin intervention reduces aflatoxin DNA adducts in individuals at high risk for liver cancer," *PNAS* 98(20):1'4601-14606 and Abstract (2001).

Goova et al., "Blockade Receptor for advanced Glycation End-Products Restores Effective Wound Healing in Diabetic Mice," *Am. Journal of Pathology*, 159(2):1 (2001).

Heggers et al., "Effect of the combination of *Aloe vera*, nitroglycering and L-NAME on Wound healing in the rat excisional model," *J. Alters. Complement Med.* 3(2):149-53 (1997).

Khanna et al., "Dermal wound healing properties of redox-active grape seed proanthocyanidins," *Free Radical Biology and Medicine* 33(8):1089:1096, Abstract, and p. 2 (2002).

Ng et al., "Plants Beneficial to the Aging Brain," *Neuroembryol Aging* 3:136-141, Abstract and p. 1 (2006).

Pickup et al., "Inflammation and Activated Innate Immunity in the Pathogenesis of Type 2 Diabetes," *Diabetes Care* 27:813-823, and p. 1 (2004).

Waller et al., "A chemical investigation of *Aloe barbadensis* miller," *Proc. Okla. Acad. Sci.*, 58:69-76 and p. 1 (1978).

International search report from corresponding PCT/US07/70368 dated Nov. 21, 2007.

Written Opinion from corresponding PCT.US07/70368 dated Nov. 21, 2007.

International Preliminary Report on Patentability from corresponding PCT.US07/70368 dated Dec. 3, 2008.

* cited by examiner

FIG. 1A
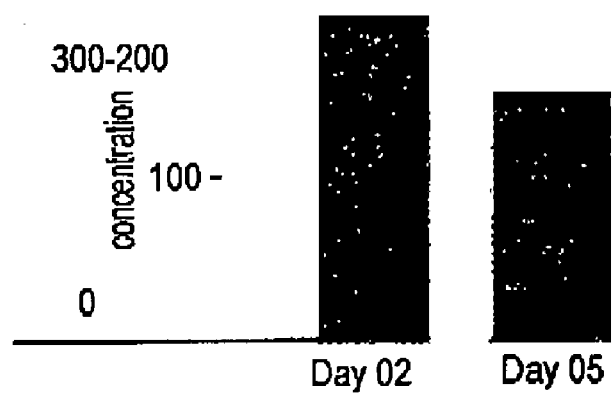
FIG. 1B
FIG. 1C
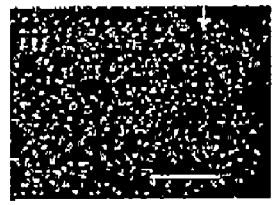
FIG. 1D
FIG. 1E
FIG. 1F

NUTRACEUTICAL TREATMENTS FOR DIABETIC AND NON-DIABETIC WOUND HEALING

This application claims benefit of priority from Provisional application Ser. No. 60/809,542 filed May. 31, 2006 and Ser. No. 60/810,741 filed Jun. 2, 2006

FIELD OF THE INVENTION

The invention relates to proposed nutraceutical treatments for aiding in wound healing in diabetic and non-diabetic patients.

BACKGROUND OF THE INVENTION

Skin is the largest organ of the human body, weighing approximately 10 pounds and covering an area of about 16 square feet. Skin is responsible for protecting the internal organs from the external world. Skin protects the body from heat, cold and physical injuries. It also provides sensory information about the nature of the external world and is the first defense against invasion by bacteria, viruses and other noxious compounds. The skin is also an excretory organ, disposing of wastes from the body in order to maintain homeostasis.

The epidermis is a stratified squamous epithelium forming the barrier that excludes harmful microbes and retains body fluids. To perform these functions, proliferative basal cells in the innermost layer periodically detach from an underlying basement membrane of extracellular matrix, move outward and eventually die. Once suprabasal, cells stop dividing and enter a differentiation program to form the barrier. The mechanism of stratification is poorly understood. Although studies in vitro have led to the view that stratification occurs through the delamination and subsequent movement of epidermal cells, most culture conditions favor keratinocytes that lack the polarity and cuboidal morphology of basal keratinocytes in tissue. These features could be important in considering an alternative mechanism that stratification occurs through asymmetric cell divisions in which the mitotic spindle orients perpendicularly to the basement membrane.

The primary function of normal intact skin is to control microbial populations that reside on the skin surface and to prevent underlying tissue from becoming invaded by pathogens (Bowler, P. G., et al., "Wound Microbiology and Associated Approaches to Wound Management," *Clinical Microbiology Reviews*, 244-269, April 2001, which is herein expressly incorporated by reference in its entirety). Since wound colonization is often microbial involving pathogenic microorganisms, a wound left untreated can become infected. Wounds can be categorized as either acute or chronic. Acute wounds are caused by external damage to intact skin and include surgical wounds, bites, minor cuts and abrasions, and more severe traumatic wounds such as lacerations and gun shot wounds. Chronic wounds are generally caused by endogenous mechanisms due to a predisposition that compromises the integrity of the dermal and epidermal tissue.

Oxygen's Role in Wound Healing

Reports from Jacques Cousteau's divers that they healed wounds significantly better when they lived in an undersea habitat about 35 feet under the surface of the Red Sea stimulated interest in the role of oxygen in wound healing (Hunt, T. K., et al., "Oxygen: at the foundation of wound healing-introduction," *World Journal of Surgery*, 28:291-293, 2004 which is herein expressly incorporated by reference in its entirety). Further research led to the consensus that limited supply of oxygen to the wound site represents a key factor for healing. Recent research substantiates that, in biological tissues, oxygen generates reactive derivatives commonly referred to as Reactive Oxygen Species (ROS).

Disrupted vasculature limits the supply of oxygen to the wound-site. Compromised tissue oxygenation or wound hypoxia is viewed as a major factor that limits the healing process as well as wound disinfection. However, oxygen also fuels tissue regeneration, as well as the oxygen-dependent respiratory burst, which is a primary mechanism to resist infection.

Wound healing commences with blood coagulation followed by infiltration of neutrophils and macrophages at the wound site to destroy pathogenic organisms through the release of ROS by an oxygen-consuming respiratory burst. The wound-site has two clear sources of ROS: (i) transient delivery of larger amounts by respiratory burst of phagocytic cells; and (ii) sustained delivery of lower amounts by enzymes present in cells such as the fibroblasts, keratinocytes and endothelial cells. At low concentrations, ROS may serve as signaling messengers in the cell and regulate numerous signal transduction and gene expression processes. Inducible ROS generated in some non-phagocytic cells are implicated in mitogenic signaling.

Diabetes Mellitus

Diabetes mellitus is a group of diseases characterized by high levels of blood glucose resulting from defects in insulin production, insulin action, or both. Diabetes can be associated with serious complications and premature death, but people with diabetes can take steps to control the disease and lower the risk of complications.

There are three main types of diabetes: Type I, Type II and Gestational diabetes. Type I diabetes was previously called insulin-dependent diabetes mellitus (IDDM) or juvenile-onset diabetes. Type I diabetes develops when the body's immune system destroys pancreatic beta cells, the only cells in the body that make the hormone insulin that regulates blood glucose. This form of diabetes usually strikes children and young adults, although disease onset can occur at any age. Type I diabetes may account for 5 percent to 10 percent of all diagnosed cases of diabetes. Risk factors for type I diabetes may include autoimmune, genetic and environmental factors.

Type II diabetes was previously called non-insulin-dependent diabetes mellitus (NIDDM) or adult-onset diabetes. Type II diabetes may account for about 90 percent to 95 percent of all diagnosed cases of diabetes. It usually begins as insulin resistance, a disorder in which the cells do not use insulin properly. As the need for insulin rises, the pancreas gradually loses its ability to produce insulin. Type II diabetes is associated with older age, obesity, family history of diabetes, history of gestational diabetes, impaired glucose metabolism, physical inactivity, and race/ethnicity. African Americans, Hispanic/Latino Americans, American Indians, and some Asian Americans and Native Hawaiians or other Pacific Islanders are at particularly high risk for type II diabetes. Type II diabetes is increasingly being diagnosed in children and adolescents.

Gestational diabetes is a form of glucose intolerance that is diagnosed in some women during pregnancy. Gestational diabetes occurs more frequently among African Americans, Hispanic/Latino Americans and American Indians. It is also more common among obese women and women with a family history of diabetes. During pregnancy, gestational diabetes requires treatment to normalize maternal blood glucose levels to avoid complications in the infant. After pregnancy, 5 percent to 10 percent of women with gestational diabetes are found to have type II diabetes. Women who have had gestational diabetes have a 20 percent to 50 percent chance of developing diabetes in the next 5 to 10 years.

Other specific types of diabetes result from specific genetic conditions (such as maturity-onset diabetes of youth), surgery, drugs, malnutrition, infections and other illnesses. Such types of diabetes may account for 1 percent to 5 percent of all diagnosed cases of diabetes Over 20 million people or 7 percent of the US population have diabetes, of which only an estimated 14.2 million have been diagnosed with the disease (American Diabetes Association). To survive, people with type I diabetes must have insulin delivered by injections or a pump. Many people with type II diabetes can control their blood glucose by following a careful diet and exercise program, losing excess weight and taking oral medication. Many people with diabetes also need to take medications to control their cholesterol and blood pressure. Diabetes self-management education is an integral component of medical care. Among adults with diagnosed diabetes, 12 percent take both insulin and oral medications, 19 percent take insulin only, 53 percent take oral medications only and 15 percent do not take either insulin or oral medications.

Diabetes and Wound Healing

About 60 percent to 70 percent of people with diabetes have mild to severe forms of nervous system damage. The results of such damage include impaired sensation or pain in the feet or hands, slowed digestion of food in the stomach, carpal tunnel syndrome and other nerve problems. Severe forms of diabetic wounds are a major contributing cause of lower-extremity amputations.

Diabetes can affect many parts of the body and can lead to serious complications such as blindness, kidney damage and lower-limb amputations. Working together, people with diabetes and their health care providers can reduce the occurrence of these and other diabetes complications by controlling the levels of blood glucose, blood pressure and blood lipids, and by receiving other preventive care practices in a timely manner. Research studies in the United States and abroad have found that improved glycemic control benefits people with either type I or type II diabetes (Collins, N., "Diabetes, Nutrition, and Wound Healing," *Advances in Skin and Wound Care,* 291-294, November 2003, which is herein expressly incorporated by reference in its entirety). In general, for every 1 percent reduction in results of glycosylated hemoglobin A1C (A1C) blood tests (e.g., from 8 percent to 7 percent), the risk of developing microvascular diabetic complications (eye, kidney and nerve disease) is reduced by 40 percent. Blood pressure control can reduce cardiovascular disease (heart disease and stroke) by approximately 33 percent to 50 percent and can reduce microvascular disease (eye, kidney and nerve disease) by approximately 33 percent. In general, for every 10 millimeters of mercury (mm Hg) reduction in systolic blood pressure, the risk for any complication related to diabetes is reduced by 12 percent. Improved control of cholesterol or blood lipids (for example, HDL, LDL and triglycerides) can reduce cardiovascular complications by 20 percent to 50 percent.

U.S. Pat. No. 5,047,249, which is expressly incorporated herein by reference in its entirety, describes compositions and methods for treating skin conditions and promoting wound healing. U.S. Pat. No. 5,487,899, which is expressly incorporated herein by reference in its entirety, describes wound healing compositions. U.S. Pat. No. 6,579,543, which is expressly incorporated herein by reference in its entirety, describes compositions for topical application to the skin.

SUMMARY OF THE INVENTION

In various embodiments of the invention, delivery or systemic presence of reactive oxygen species (ROS) at the wound site can be used to not only disinfect the wound but directly facilitate the healing process. In an embodiment of the invention, delivery or systemic presence of ROS play a direct role in facilitating angiogenesis by inducing VEGF expression in wound-related cells such as keratinocytes and macrophages. In an embodiment of the invention, a composition consisting of one or more compounds of zinc, chromium, berry extract, *Polygonum cuspidatum* extract, L-arginine, aloe vera and chlorophyll is administered orally or topically to reduce inflammation, improve wound healing, improve innervation of regenerative tissue, improve healing of excisional wounds and prevent neurodegeneration in a mammal.

In one aspect the mammal is suffering from diabetes mellitus. It is further contemplated that a composition consisting of one or more compounds of zinc, chromium, berry extract, *Polygonum cuspidatum* extract, L-arginine, aloe vera and chlorophyll administered orally or topically to a mammal is used to treat diabetes and one or more of inflammation, slow wound healing, lack of innervation of regenerative tissue, slow healing of excisional wounds and neurodegeneration.

Nutritional factors play a key role in determining wound outcomes in diabetic and non-diabetic wound healing. In an embodiment of the present invention, an optimum nutraceutical formula with one or more compounds of chromium, zinc, berry extract, *Polygonum cuspidatum* extract, L-arginine, aloe vera and chlorophyll has a synergistic beneficial effect on inflammation, wound healing and neuro-regeneration. Wound healing, inflammation and neuro-regeneration can be evaluated orally and topically in both diabetic and non-diabetic mice at various human equivalent doses. L-arginine at human equivalent doses can be used as a positive control.

Just hours after injury, the wound site recruits inflammatory cells. MCP-1 deficient mice recruit fewer phagocytic macrophages to the injury site. In addition, macrophages that are recruited suffer from compromised functionality. MCP-1 is angiogenic in vivo. At the wound site, macrophages deliver numerous angiogenic products including $H_2O_2$. This observation, taken together with the result that topical $H_2O_2$ facilitates dermal wound healing, point towards a clear role of $H_2O_2$ as a messenger for dermal wound healing (Roy, S. et al., "Dermal wound healing I subject to redox control," *Molecular Therapy* 13, 211-220, 2006, which is herein expressly incorporated by reference in its entirety). Over the counter, $H_2O_2$ is commonly available at strength of 3%. Historically, at such strength $H_2O_2$ has been clinically used for disinfection of tissues. The use of $H_2O_2$ to disinfect wounds continues today with a valid concern that at such high doses $H_2O_2$ may hurt nascent regenerating tissues. Indeed, no beneficial effect of 3% $H_2O_2$ has been observed.

It is provided that each of the conditions contemplated in the methods of the invention, e.g., reduced inflammation, improved wound healing, improved innervation of regenerative tissue, improved healing of excisional wounds and prevention of neurodegeneration in a mammal, may be treated with any of the chromium, berry extract, zinc, trans-Resveratrol, L-arginine, aloe vera or chlorophyllin compounds or substances set out below. All of the compounds listed below are described in general terms.

For example, chromium can come from chromium nicotinate, chromium polynicotinate, chromium chloride, chromium picolinate, etc. Zinc can come from zinc methionine, zinc gluconate, zinc oxide, zinc acetate, etc.

Chromium an essential trace mineral required for normal insulin function and glucose homeostasis. Chromium has been shown to help prevent the buildup of plaque in arteries by lowering harmful low-density lipoprotein (LDL) cholesterol and increasing beneficial high-density lipoprotein (HDL) cholesterol. It also helps to maintain healthy body weight and normal blood pressure. In addition to blood sugar regulation, insulin is important for protein synthesis in tissue regeneration. During pregnancy, a significant amount of chromium is transported across the placental barrier for the growing fetus, which may be a causative factor for gestational diabetes.

Berry extracts are rich in anthocyanins, which are known to act as mild prooxidants in wounds and help in wound healing. Anthocyanins also serve as antioxidants, scavengers of free radicals which protect surrounding tissues from phagocytic respiratory bursts and serve as inhibitors of neoplastic processes. In an eight-week study, animals fed OPTIBERRY®, a combination of six standardized berry anthocyanin extracts, and exposed to oxidative stress showed significant whole-body antioxidant protection as compared with control animals. It is contemplated that berry extracts can be from one or more berries selected from the group consisting of blueberry, bilberry, elderberry, cranberry, strawberry, raspberry, blackberry and wolfberry. In a related embodiment, the berry extract further comprises anthocyanins.

Zinc is a an essential trace mineral and a constituent of the hormone insulin. Zinc is also involved in skin and connective tissue metabolism and in wound healing. Zinc monothionine, a highly bioavailable form of zinc, has been shown to reduce excess levels of free radicals produced by white blood cells, therefore protects the body against free radicals and free radical-induced lipid peroxidation and DNA damages. It is contemplated that the zinc can be selected from the group consisting of zinc methionine, zinc sulfate, zinc polyascorbate, zinc oxide, zinc histidine, zinc gluconate, zinc citrate, zinc acetate, zinc picolinate, zinc alpha-ketoglutarate and zinc aspartate.

trans-Resveratrol is an all-natural phytochemical present in extracts of *Polygonum cuspidatum*. In vitro and in vivo studies have shown that trans-resveratrol possesses many biological attributes that favor cardio protection, antioxidant activity, modulation of hepatic lipid synthesis and inhibition of platelet aggregation, as well as inhibition of pro-atherogenic eicosanoids by human platelets and neutrophils. Trans-Resveratrol has been shown to be a potential chemo preventive agent by inhibiting the cellular events associated with tumor initiation, promotion and progressions. Resveratrol can directly stimulate cell proliferation and differentiation of osteoblasts and decrease tumor growth in vivo. In one aspect, the *Polygonum cuspidatum* extract further comprises trans-resveratrol. In a related aspect, the *Polygonum cuspidatum* extract is substituted by alternate sources of trans-resveratrol L-arginine has been shown to enhance wound breaking strength and collagen deposition in rodents and humans. Diabetes mellitus, which impairs wound healing, is accompanied by a reduction in nitric oxide at the wound site. The amino acid L-arginine is the only substrate for nitric oxide synthesis. Impaired healing of diabetic wounds can be partially corrected by L-arginine supplementation.

Aloe Vera is known to promote wound healing and is widely effective in treating assortment of skin diseases. Of the 200 plus species of aloe vera, aloe *Barbendisis miller* is the most common. It is shown to stimulate repair process and epidermal growth, and to stimulate fibroblast and connective tissue formation, promoting wound repair. Many believe that aloe provides a barrier over the wound to speed the wound healing process. Its active ingredients are anthraquinones, resin, tannins, polysaccharides, prostaglandins and fatty acids. In one aspect, the invention provides methods wherein the aloe vera further comprises aloe *Brabendisis miller*.

Chlorophyllin a and Chlorophyllin b are natural, fat-soluble chlorophylls found in plants. The basic structure of chlorophyll is a porphyrin ring similar to that of heme in hemoglobin. Chlorophyllin is a semi-synthetic mixture of water-soluble sodium copper salts derived from chlorophyll. Chlorophyllin has been used orally as an internal deodorant and topically in the treatment of slow-healing wounds for more than 50 years without any serious side effects. Chlorophyllin can neutralize several physically relevant oxidants in vitro, and limited data from animal studies suggest that chlorophyllin supplementation may decrease oxidative damage induced by chemical carcinogens and radiation. Research in the 1940s indicating that chlorophyllin solutions slowed the growth of certain anaerobic bacteria in the test tube and accelerated the healing of experimental wounds in animals led to the use of topical chlorophyllin solutions and ointments in the treatment of persistent open wounds in humans. During the late 1940s and 1950s, a series of largely uncontrolled studies in patients with slow-healing wounds, such as vascular ulcers and pressure (decubitus) ulcers, reported that the application of topical chlorophyllin promoted healing more effectively than other commonly used treatments. In the late 1950s, chlorophyllin was added to papain and urea-containing ointments used for the chemical debridement of wounds in order to reduce local inflammation, promote healing and control odor. Chlorophyllin-containing papain/urea ointments are still available in the US by prescription. In one embodiment of the methods of the invention, the chlorophyllin can be selected from water soluble chlorophyllin, sodium chlorophyllin, copper chlorophyllin, fat soluble chlorophyll A and fat soluble chlorophyll B.

In a further embodiment, the invention provides a composition for administration to reduce inflammation, improve wound healing, improve innervation of regenerative tissue, improve healing of excisional wounds and prevent neurodegeneration in a mammal comprising an amount of chromium between: a lower limit of approximately 10 µg human equivalency dosage (HED) per day; and an upper limit of approximately 1000 µg HED per day; an amount of zinc between: a lower limit of approximately 1.5 mg HED per day; and an upper limit of approximately 75 mg HED per day; an amount of berry extract between a lower limit of approximately 3 mg HED per day; and an upper limit of approximately 500 mg HED per day; an amount of *Polygonum cuspidatum* extract between: a lower limit of approximately 1.5 mg HED per day; and an upper limit of approximately 100 mg HED per day; an amount of trans-resveratrol between: a lower limit of approximately 0.1 mg HED per day; and an upper limit of approximately 50 mg HED per day; an amount of l-arginin between: a lower limit of approximately 50 mg HED per day; and an upper limit of approximately 1000 mg HED per day; an amount of chlorophyllin between: a lower limit of approximately 10 mg HED per day and an upper limit of approximately 300 mg HED per day.

In a related aspect, the invention provides a composition for topical application to reduce inflammation, improve wound healing, improve innervation of regenerative tissue, improve healing of excisional wounds and prevent neurodegeneration in a mammal. In one embodiment the composition above is for topical application and further comprises: an amount of aloe *Barbendisis miller* between: a lower limit of approximately 0.01% (by weight) and an upper limit of approximately 10% (by weight). In a related embodiment, the composition for topical application comprises an amount of chromium between: a lower limit of approximately 0.01% (by weight) and an upper limit of approximately 10% (by weight); an amount of zinc between: a lower limit of approximately 0.01% (by weight) and an upper limit of approximately 10% (by weight); an amount of berry extract between: a lower limit of approximately 0.01% (by weight)and an upper limit of approximately 10% (by weight); an amount of *Polygonum cuspidatum* extract between: a lower limit of approximately 0.01% (by weight) and an upper limit of approximately 10% (by weight); an amount of trans-resveratrol between: a lower limit of approximately 0.01% (by weight) and an upper limit of approximately 10% (by weight); an amount of L-arginine between: a lower limit of approximately 0.01% (by weight) and an upper limit of approximately 10% (by weight); an amount of aloe *Barbendisis miller* between: a lower limit of approximately 0.01% (by weight) and an upper limit of approximately 10% (by weight); an amount of chlorophyllin between: a lower limit of approximately 0.01% (by weight) and an upper limit of approximately 5% (by weight).

BRIEF DESCRIPTION OF DRAWINGS

FIG. 1A shows plot of wound area as a % of initial wound for diabetic versus non-diabetic mice;

FIG. 1B shows hematoxylin and eosin staining of the wounds on diabetic mouse day 3, post wounding;

FIG. 1C shows hematoxylin and eosin staining of the wounds on non-diabetic mouse day 3, post wounding;

FIG. 1D shows TUNEL staining of the wounds on diabetic mouse day 3, post wounding;

FIG. 1E shows plot of apoptotic cells for diabetic (NOR) versus non-diabetic (NOD) mice; and FIG. 1F shows individual macrophage stained with anti-F4/80 coupled with FITC and counterstained with blue.

DETAILED DESCRIPTION OF THE INVENTION

Phase I: In Vivo Dose-Response Study

The effect of one or more compounds of zinc, chromium, berry extract, *Polygonum cuspidatum* extract, L-arginine, aloe vera and chlorophyllin on wound healing and inflammation can be evaluated orally and topically in both diabetic and non-diabetic mice (six animals per group) at various Human Equivalent Doses Oral HED=(oral animal dosage)×(Human weight/animal weight)$^{1/3}$, topical HED=topical animal dosage. L-arginine at human equivalent doses can be used as a positive control.

The average weight for male adults in the United States is about 76-83 Kg. The average weight for female adults in the United States is about 54-64 Kg. The average weight for mice is 20 gm. Thus, the conversion equations for oral Human Equivalent Dosage to mice dosages are approximately oral HED=15×oral mice dosage. Topical HED=topical animal dosage.

Test Groups:

Group A—Diabetic Oral (Taken 1-3 Months Before Wounding)

Diabetic Mice Control
Elemental chromium at 10, 50, 100, 200, 400 and 1000 μg human equivalency dosages;
Elemental zinc at 1.5, 7.5, 15, 25, 50 and 75 mg human equivalency dosages;
Berry extract at 3, 10, 50, 100, 250 and 500 mg human equivalency dosages;
*Polygonum cuspidatum* extract standardized to 50% trans-resverat at 1, 5, 10, 25, 50 and 100 mg human equivalency dosages;
L-Arginine at 10, 100, 500, 1,000, 5,000 and 10,000 mg human equivalency dosages;
Chlorophyllin (sodium copper salts of chlorophyll) at 10, 50, 100, 150, 200, 250 and 300 mg human equivalency dosages.

Group B—Non-Diabetic Oral (Taken 1-3 Months Before Wounding)

Non-Diabetic Mice Control
Elemental chromium at 10, 50, 100, 200, 400 and 1000 μg human equivalency dosages;
Elemental zinc at 1.5, 7.5, 15, 25, 500 and 75 mg human equivalency dosages;
Berry extract at 3, 10, 50, 100, 250 and 500 mg human equivalency dosages;
*Polygonum cuspidatum* extract standardized to 50% trans-resveratrol at 1, 5, 10, 25, 50
and 100 mg human equivalency dosages
L-Arginine at 10, 100, 500, 1,000, 5,000 and 10,000 mg human equivalency dosages;
Chlorophyllin (sodium copper salts of chlorophyll) at 10, 50, 100, 150, 200, 250 and 300 mg human equivalency dosages.

Initial pilot studies can be conducted in all treatment groups using the highest oral doses. The objective of experiments proposed under this section is to characterize wound healing in type II diabetes. Specifically, studies can be focused on whether these mice have a prolonged inflammatory phase, as has been suggested to be a leading cause of most non-healed wounds in diabetics. For example, mice can be fed a diet consisting of one or more compounds of 67 μg elemental chromium, 5 mg elemental zinc, 33 mg berry extract, 16.7 mg *Polygonum cuspidatum* extract, 67 mg L-arginine and 20 mg chlorophyllin for 4-12 weeks prior to inflicting the wound. Alternatively, mice can be topically treated twice daily for 30 days after wounding using a cream or gel on their wound comprising one or more of 0.01 wt % to 10 wt % of chromium, 0.01 wt % to 10 wt % of zinc, 0.01 wt % to 10 wt % of berry extracts, 0.01 wt % to 10 wt % of *Polygonum cuspidatum* extract, 0.01 wt % to 10 wt % of L-arginine, 0.01 wt % to 10 wt % of aloe *Barbendisis miller*, and 0.01 wt % to 5 wt % of chlorophyllin.

Blood glucose levels can be monitored weekly by obtaining blood from tail-nick and using a glucometer (Elite system, Bayer). The animals can be used after 3-4 weeks of blood glucose reaching the 250 mg/dL level. Wound healing can be assessed according to the following criteria:

A. Wound Closure.

For wound closure and contraction studies, two full thickness (5×10 mm) excisional wounds can be placed on the dorsum of male 8-10 wks db/db (Chen, H. et al., "Evidence that the Diabetes Gene Encodes the Leptin Receptor: Identification of a mutation in the Leptin Receptor Gene in db/db Mice," *Cell*, 84:491-495, 1996, which is herein expressly incorporated by reference in its entirety) as well as the corresponding (age and sex matched) control (heterozygous, db/+) mice. Wound area can be measured by imaging wounds every alternate day post wounding using a digital camera (Canon Powershot G6) and a reference scale. Wound area from the images can be calculated using WoundMatrix™ software.

B. Histology

For histology, two 3 mm full thickness punch biopsy wounds can be made. The entire wound can be harvested using a 6 mm punch biopsy. One of the two wounds can be formalin fixed and paraffin embedded, while the other one can be collected frozen in OCT followed by sectioning using a microtome (or crymicrotome for frozen sections). To visualize general wound architecture, the sections can be stained with hematoxylin-eosin (HE) and Masson Trichrome.

Inflammation.

The inflammatory phase can be characterized by quantifying the number of mEI and neutrophil in histological sections on specific days (0, 1, 3, 5, 7 d) following wounding. The cells can be detected using standard immuno-staining protocol and the following detection antibody (in parentheses): mU (MOMA-2, F4/80, Macl) and neutrophils (Anti-Ly-6G, anti-neutrophil). The number of mil or neutrophils within a section can be enumerated on five visual fields under high magnification (40×). Laser Doppler wound blood flow imaging. Establishment of proper blood flow is a marker of successful regeneration of tissue at the wound site. Wound blood flow imaging can be performed by Doppler blood flow imager (Moor Instruments) that offers a high spatial resolution. Expected results, potential problems, and solutions. Based on previous studies, it is anticipated that diabetics exhibit an impaired wound closure as compared to their corresponding controls. Choice of proper control with each model is critical for proper interpretation of the data obtained. Age and gender-matched heterozygous (dbl+) mice as control. The heterozygotes show normal body weight, blood glucose and plasma insulin. Because of compromised leukocyte function, diabetic mice are susceptible to infections. Routine checks for the presence of microbial flora in wounds of diabetic and non-diabetic mice can be carried out to assess that the observed differences are not merely due to difference in wound microflora.

Migration/Transportation of Chromium, Zinc, Berry Extract, *Polygonum cuspidatum* Extract, Aloe Vera and Chlorophyllin Chlorophyllin or L-arginine to the subcutaneous or dermal tissue following oral administration can be assessed at 30 and 90 days of treatment, and quantified by HPLC. Based on these results, two additional oral doses can be selected from the above list for all treatment groups and migration/transportation of chromium, zinc, berry extract, *Polygonum cuspidatum* extract, L-arginine, aloe vera and chlorophyllin to the subcutaneous or dermal tissue can be quantified by HPLC at 30 and 90 days of treatment. All the Test Parameters (itemized below) can be evaluated in all groups.

Based on the results obtained in Groups A and B, and the available concentrations of similar active components in the creme/topical formulations in the marketplace, 3 doses are selected for topical application for each product. A suitable vehicle is a hydrophilic based jelly. Alternative vehicles to a hydrophilic based jelly are also within the spirit of this invention. All the Test Parameters (itemized below) can be evaluated in all groups.

Group C—Diabetic Topical (Applied Twice Daily Up to 30 Days After Wounding)

Diabetic Mice Control
Elemental chromium: 0.01-10% weight percent;
Elemental zinc: 0.01-10% weight percent;
Berry extract: 0.01-10% weight percent;
*Polygonum cuspidatum* extract: 0.01-10% weight percent;
L-arginine: 0.01-10% weight percent;
Aloe *Barbendisis miller:* 0.01-10% weight percent;
Chlorophyllin (sodium copper salts of chlorophyll): 0.01-5% weight percent Group D—Non-Diabetic Topical (Applied Twice Daily for 30 Days After Wounding)

Non-Diabetic Mice Control
Elemental chromium: 0.01-10% weight percent;
Elemental zinc: 0.01-10% weight percent;
Berry extract: 0.01-10% weight percent;
*Polygonum cuspidatum* extract: 0.01-10% weight percent;
L-Arginine: 0.01-10% weight percent;
Aloe *Barbendisis miller:* 0.01-10% weight percent;
Chlorophyllin (sodium copper salts of chlorophyll): 0.01-5% weight percent Test Parameters:
 1. Wound Healing:
  a. Acceleration of wound healing (before and after picture)
  b. Angiogenesis
  c. Immuno-histochemistry/scarring
  d. Glutathione
  e. Inflammation markers (TNFα, Cytokines)
  f. Healing related genes
  g. Nerve damage markers
  h. Glucose/insulin markers Phase II: In Vivo Combinations Based on Phase I results, as well as ingredient cost considerations, various combinations and concentrations of ingredients can be formulated and re-tested in both diabetic and non-diabetic mice (six animals per group) according to the same test parameters in Phase I to determine the safest and most effective combinations in vivo.

Formulations:

Formulations designed for oral administration shall consist of two or more of the following compounds: zinc, chromium, berry extract, *Polygonum cuspidatum* extract, aloe vera, chlorophyllin and L-arginine.

Formulations can be designed for topical application shall consist of two or more of the following compounds: zinc, chromium, berry extract, *Polygonum cuspidatum* extract, aloe vera, chlorophyllin and L-arginine.

EXAMPLE 1

Wound healing is impaired in type I diabetic mice. To determine the effect of the compositions described herein on wound healing in diabetic mammals, two full-thickness excisional wounds were placed on the dorsal skin of diabetic NOD/LtJ mice and matched control non-obese non-diabetic NOR/LtJ mice (12-15 wks, 5×10 mm wounds).

Results are shown in FIG. 1A. Wound area is shown as % of area of initial wound. Data are shown as mean±SD (n=4)*, $p<0.05$ versus corresponding non-diabetic control mice. As shown in FIG. 1B-FIG. 1C, histological analyses using hematoxylin and eosin staining of the wounds on day 3, post wounding, clearly demonstrated increased cellularity in NOD wounds versus NOR wounds (Scale bar=100 μm).

To visualize dead cells in the wound tissue, deoxynucleotidyl transferase-mediated dUTP nick end labeling (TUNEL) staining was optimized. Stained images show (FIG. 1D) a positive control that was generated by treating the tissue section treated with proteinase K and nuclease. TUNEL positive apoptotic cells can be seen with black nuclear stain (Scale bar=100 pm) (FIG. 1E). Results of TUNEL positive cell scoring show that the number of dead cells in the wound tissue was higher in wound tissue (d 3 post wounding). Data shown are mean±SD (n=3), $p<0.05$ compared to NOR animals.

PVA sponges were implanted subcutaneously on the back of NOD and NOR animals. The sponges were harvested on d 5 of implantation and the cells were sorted through magnetic sorting to isolate pure macrophage (mϕ, F4 180 positive) population from the PVA sponge cell suspension. Mϕ suspension was then cytospun. Individual macrophage stained using anti-F4/80 coupled with FITC (green) and counterstained using DAPI (blue) (Scale bar=10 μm) (FIG. 1F). The F4/80 staining of wound mϕ cytospin showed over 98% pure mϕ population after the magnetic sorting thus establishing efficacy of this technique.

Mice homozygous (BKS.Cg−m+1+Lepr') for spontaneous mutation of the leptin receptor (Lepr") become identifiably obese around 3 to 4 weeks of age. Elevation of blood sugar is evident at 4 to 8 weeks after birth.

Blood glucose levels were monitored weekly by obtaining blood from tail-nick and using a glucometer (Elite system, Bayer). The animals were analyzed 3-4 weeks after blood glucose reached the 250 mg/dL level.

These results suggest that future studies can be focused on whether these mice have a prolonged inflammatory phase, as has been suggested to be a leading cause of most non healed wounds in diabetics.

Wound Healing in Diabetic Mice

Wound healing can be assessed according to the following criteria:

A. Wound Closure.

For wound closure/contraction studies, two full thickness (5×10 mm) excisional wounds can be placed on the dorsum of male 8-10 wks db/db as well as the corresponding (age and sex matched) control (heterozygous, db/+) mice. Wound area can be measured by imaging wounds every alternate day post wounding using a digital camera (Canon Powershot G6) and a reference scale. Wound area from the images can be calculated using WOUNDMATRIX™ software.

B. Histology.

For histology, two 3 mm full thickness punch biopsy wounds can be made. The entire wound can be harvested using a 6 mm punch biopsy. One of the two wounds can be formalin fixed and paraffin embedded while the other one can be collected frozen in OCT followed by sectioning using a microtome (or crymicrotome for frozen sections). To visualize general wound architecture, the sections can be stained with hematoxylin-eosin (HE) and Masson Trichrome.

C. Inflammation.

The inflammatory phase can be characterized by quantifying the number of mϕ and neutrophil cells in histological sections on specific days (0, 1, 3, 5, 7 day) following wounding. The cells can be detected using standard immuno-staining protocols and the following detection antibody: mϕ (MOMA-2, F4/80, Macl) and neutrophils (Anti-Ly-6G, anti-neutrophil). The number of mϕ or neutrophils within a section can be enumerated on five visual fields under high magnification (40×).

D. Laser Doppler Wound Blood Flow Imaging.

Establishment of proper blood flow is a marker of successful regeneration of tissue at the wound site. Wound blood flow imaging can be performed by Doppler blood flow imager (Moor Instruments) that offers a high spatial resolution.

Expected Results, Potential Problems and Solutions

Based on previous studies, it is anticipated that diabetic patients show an impaired wound closure as compared to their corresponding controls. Choice of proper control with each model is critical for proper interpretation of the data obtained. Age and gender-matched heterozygous (dbl+) mice are used as control. The heterozygotes show normal body weight, blood glucose, and plasma insulin. Because of compromised leukocyte function, diabetic mice are susceptible to infections. The presence of microbial flora in wounds of diabetic and non-diabetic mice is checked to assess that the observed differences are not merely due to difference in wound microflora.

Wound Models

A. Secondary-intention Excisional Dermal Wound Model.

Wounding of mice is performed after anesthetized with isoflurane inhalation. For wound contraction (closure) and biochemical (RNA, protein etc.) studies, two 5×10 mm full-thickness (skin and panniculus carnosus) excisional wounds are placed on the dorsal skin (shaved and cleaned using betadine), equidistant from the midline and adjacent to the four limbs. The wounds are allowed to dry to form a scab. For wound histology studies, two 3 mm full-thickness (using a biopsy punch; skin and panniculus camosus) excisional wounds are placed on the dorsal skin (shaved and cleaned using betadine), equidistant from the midline and adjacent to the four limbs. The wounds are allowed to dry to form a scab. On the specified day of harvest, the entire wounds are harvested using a 6 mm biopsy punch. One of the wounds can be formalin fixed and paraffin embedded for histology purposes. The other wounds are collected in OCT for frozen sectioning and histology. Microbial flora in wounds is determined routinely to determine that the observed differences are not merely due to difference in wound microflora. To minimize wound infections, all mice for the experiments are housed in a sterile facility.

B. "Hunt/Schilling" Wire Mesh Cylinder for Wound Fluid Collection.

This method is used to collect wound fluid during the course of healing. The implantation of wire mesh cylinder (stainless steel; 2.5 cm length and 0.8 cm diameter) and wound fluid harvest is performed.

C. Histologic Evaluation.

Formalin-fixed paraffin embedded wound tissue blocks are sectioned using a microtome (4 μm thick). For histological evaluations, the sections are stained with hematoxylin and eosin (HE) as well as for Masson Trichrome staining. Immunostaining: Formalin-fixed paraffin-embedded or acetone fixed frozen-tissue sections or cytospins are labeled and detected with appropriate primary and secondary (HRP or fluorochrome-tagged) antibody. HRP tagged secondary antibody can be developed using DAB as substrate (brown color).

D. Laser Doppler Wound Blood Flow Imaging.

Establishment of proper blood flow is a marker of successful regeneration of tissue at the wound site. Wound blood flow imaging can be performed by Doppler blood flow imager (Moor Instruments) that offers a high spatial resolution.

E. Assessment of Microbial (Bacterial) Growth in Wounds.

Routine analyses of wound swabs normally involve the use of non-selective (e.g., LB and blood agar) and selective (e.g., MacConkey) agar plates. For the proposed studies related to wound microbiology, LB agar plates are used. For gram-negative bacteria, MacConkey agar plates are used.

F. Superficial Bacterial Load:

The entire surface of the wound can be swabbed for 20 sec using an alginate-tipped applicator. The tip of the swab is broken off and placed into sterile tube containing saline. Serial dilution of quantitative swabs is performed and plated on sterile LB agar medium. All plated specimens are incubated under aerobic conditions at 37° C. After 24 hours, the plates are visually inspected and colonies of bacteria counted. Colony forming units (CFU) are then utilized to determine the total bacterial count on each plate 6. Deep tissue bacterial load: The superficial eschar tissue is removed. Wound bed tissue underneath eschar is biopsied aseptically, weighed, homogenized, serially diluted and cultured on LB agar plates as described above. Quantitative assessment of bacterial load is determined by counting the number of colonies on each plate.

G. mRNA Quantitation.

Total RNA is extracted using Trizol (Invitrogen) and RNAeasy kit (Qiagen). Quantitative or real-time PCR (Taqman or Sybr Green) approach is used for mRNA quantification.

H. Synergism

A synergistic effect is when the effect of the sum of the entities is more than the effect of any one entity. In this field, where a multitude of factors work significantly more potently than any one factor alone, it is considered unfeasible to establish the effect of all the separate entities alone. In the present invention, it is not required that the effect of all separate entities be established and then that the effect observed is greater than the sum of the individual effects observed.

Numerous modifications and variations in the invention as set forth in the above illustrative examples are expected to occur to those skilled in the art. Consequently only such limitations as appear in the appended claims should be placed on the invention

What is claimed is:

1. A composition for administration to reduce inflammation and enhance wound healing in a mammal, the composition comprising:
   an amount of chromium between:
      a lower limit of approximately 10 µg human equivalency dosage (HED) per day; and
      an upper limit of approximately 1000 µg HED per day;
   an amount of zinc between:
      a lower limit of approximately 1.5 mg HED per day; and
      an upper limit of approximately 75 mg HED per day;
   an amount of berry extract comprising anthocyanins between:
      a lower limit of approximately 3 mg HED per day; and
      an upper limit of approximately 500 mg HED per day;
   an amount of *Polygonum cuspidatum* extract between:
      a lower limit of approximately 1.5 mg HED per day; and
      an upper limit of approximately 100 mg HED per day;
   an amount of trans-resveratrol between:
      a lower limit of approximately 0.1 mg HED per day; and
      an upper limit of approximately 50 mg HED per day;
   an amount of 1-arginin between:
      a lower limit of approximately 50 mg HED per day; and
      an upper limit of approximately 1000 mg HED per day;
   an amount of chlorophyllin between:
      a lower limit of approximately 10 mg HED per day; and
      an upper limit of approximately 300 mg HED per day.

2. The composition of claim 1 which is for topical application and further comprises:
   an amount of aloe *Barbendisis miller* between:
      a lower limit of approximately 0.01 % (by weight);
      an upper limit of approximately 10 % (by weight).

* * * * *